United States Patent [19]

Li

[11] Patent Number: 5,146,006

[45] Date of Patent: Sep. 8, 1992

[54] PROCESS FOR PREPARING TETRAPHENOIC COMPOUNDS

[75] Inventor: Simon M. Li, Houston, Tex.

[73] Assignee: Shell Oil Company, Houston, Tex.

[21] Appl. No.: 722,983

[22] Filed: Jun. 28, 1991

[51] Int. Cl.$^5$ .......................... C07C 39/12; C07C 37/20
[52] U.S. Cl. ...................................... 568/720; 528/204; 568/716; 568/718
[58] Field of Search ............... 568/716, 717, 718, 720, 568/650, 652; 528/204

[56] References Cited

U.S. PATENT DOCUMENTS

| | | | |
|---|---|---|---|
| 2,806,016 | 9/1957 | Schwarger | 260/47 |
| 3,013,088 | 12/1961 | Schwarzer et al. | 568/720 |
| 3,394,089 | 7/1968 | McNutt et al. | 260/2.2 |
| 3,972,950 | 8/1976 | Kwantes | 260/619 A |
| 4,415,724 | 11/1983 | Mark | 528/204 |
| 4,415,725 | 11/1983 | Hedges et al. | 568/720 |
| 4,584,416 | 4/1986 | Pressman et al. | 568/727 |
| 4,638,101 | 1/1987 | Rosenquist | 568/720 |
| 4,820,740 | 4/1989 | Li | 521/32 |
| 5,012,016 | 4/1981 | Li | 568/720 |

FOREIGN PATENT DOCUMENTS

| | | | |
|---|---|---|---|
| 0139533 | 12/1978 | Japan | 568/720 |
| 859456 | 1/1961 | United Kingdom | 568/720 |
| 833033 | 11/1961 | United Kingdom | 568/720 |

Primary Examiner—Werren B. Lone

[57] ABSTRACT

A process is disclosed for preparing a tetrakisphenol by the reaction of a dialdehyde with a phenolic compound in the presence of a cationic exchange resin catalyst, and then subjecting a solution of the condensation product to conditions suitable for crystallization of the polyphenolic product relatively high in the tetrakisphenol species.

116 Claims, 3 Drawing Sheets

PROCESS FOR PREPARING TETRAPHENOIC COMPOUNDS

BACKGROUND OF THE INVENTION

This invention relates to the preparation of tetraphenolic compounds. In one aspect, the invention relates to a process for preparing tetraphenolic precursors of low-chlorine epoxy resins suitable for high-performance electronics applications. In a specific embodiment, the invention relates to the preparation of the tetraphenol of ethane from glyoxal and phenol.

Tetraphenolic compounds such as the tetraphenol of ethane are starting materials for the preparation of multifunctional epoxy resins for electronics applications. The tetraphenol of ethane can be prepared by the acid-catalyzed condensation reaction of glyoxal and phenol in a homogeneous liquid reaction mixture. Typical acid catalysts include aqueous hydrochloric acid and oxalic acid. When aqueous HCl is the catalyst for the reaction, the acidic reaction product mixture is typically neutralized by addition of a base such as sodium hydroxide. The neutralized product mixture is then distilled for removal of excess phenol and by-products. The product yield of the desired tetrakis species is typically low, the reaction product being a mixture of di-, tri- and tetraphenolic isomers.

It is therefore an object of the invention to provide a process for preparing tetraphenolic compounds which permits recovery of the tetrakis phenolic species in relatively high purity. In one aspect, it is an object of the invention to provide phenolic precursors of low-chlorine epoxy resins for electronics applications.

SUMMARY OF THE INVENTION

Figure 1:
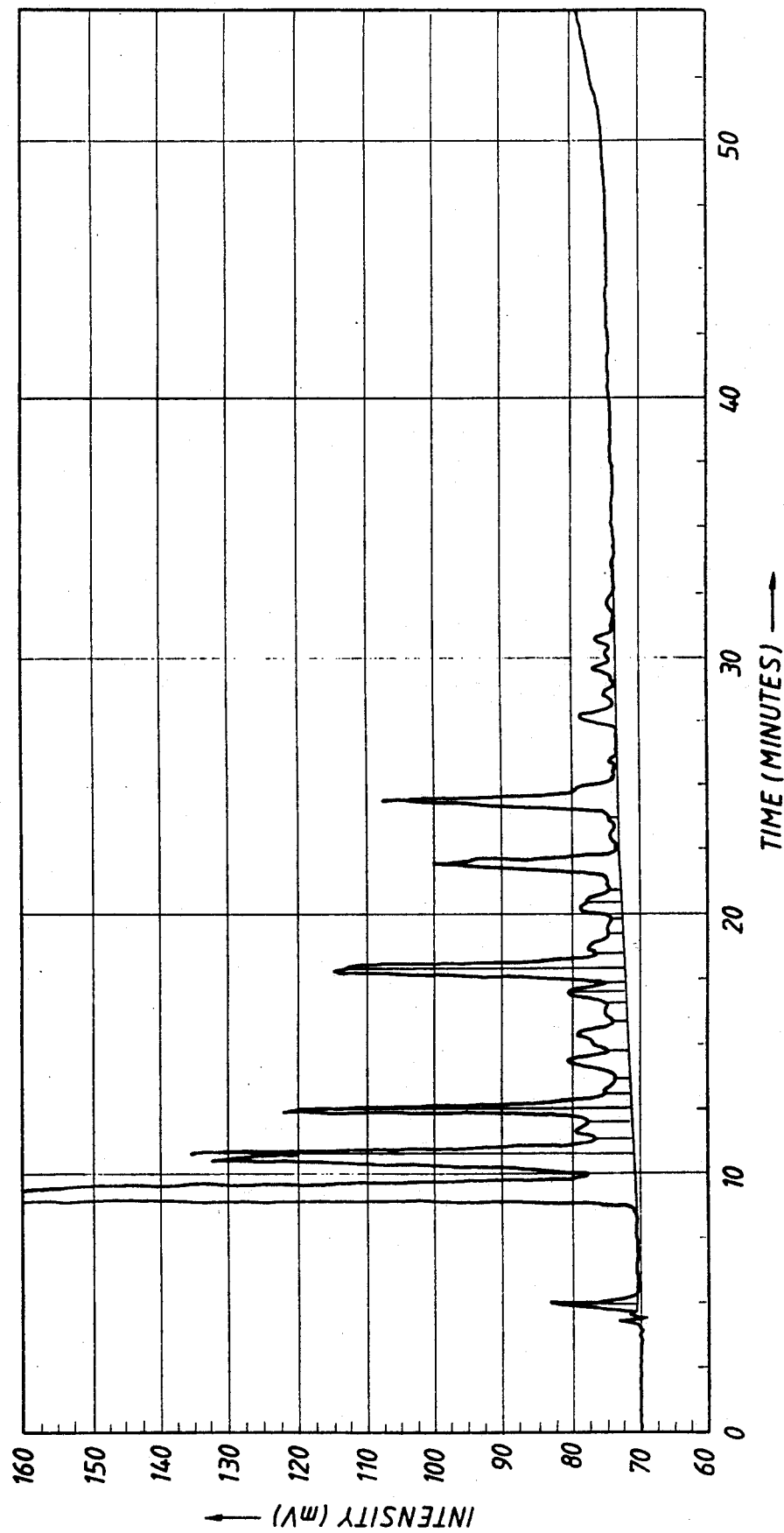
FIG. 1 is a high-performance liquid chromatogram (HPLC) of a crude polyphenolic reaction product prepared as described in Example 1.

According to the invention, a process is provided for preparing a tetrakisphenolic compound which can be described by the structural formula

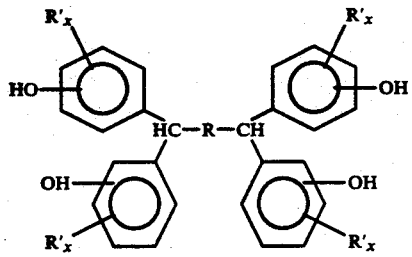

in which R can be, for example, a direct bond, $C_{1-20}$ hydrocarbyl including alkyl, aryl, and the like, each R' can be halide, $C_{1-6}$ alkyl or $C_{1-6}$ alkoxy, and x is an integer from 0 to 4, by contacting, in a reaction mixture under condensation reaction conditions, a dialdehyde with an equivalent excess of a phenol in the presence of a cationic exchange resin catalyst, and then subjecting a solution of the condensation product to conditions suitable for crystallization of a polyphenolic product relatively rich in the tetrakisphenol species. By controlling crystallization conditions, the relative amounts of the different tetrakisphenolic isomers in the product can be controlled. According to one embodiment of the invention process, the crystallization medium is the excess phenolic reactant. In an alternate embodiment, the crude product is first separated from the majority of the excess phenol present in the reaction effluent and is then crystallized from an added organic solvent. The resulting tetrakisphenol can be glycidated to produce a polyglycidyl ether which can itself be crystallized from solution to produce a very low-chlorine tetrafunctional epoxy resin.

DETAILED DESCRIPTION OF THE INVENTION

The starting materials for the condensation reaction for the preparation of the desired tetraphenolic compound are a dialdehyde and a phenolic compound. Suitable dialdehydes include compounds which can be represented by formula (1):

in which R is a direct bond or a hydrocarbyl linking moiety. R can be, for example, $C_{1-20}$ hydrocarbyl, including substituted and unsubstituted alkyl, aryl, alkaryl, aralkyl, cycloalkyl, and the like. Preferably, R is substituted or unsubstituted $C_{1-12}$ alkyl, aryl or alkaryl, particularly as represented structurally in formulas (2) and (3) below:

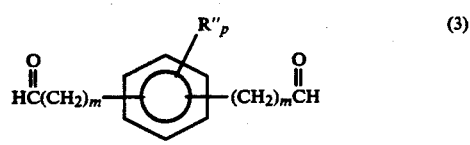

in which n is an integer from 0 to 12, m is an integer from 0 to 6, each R" is a non-interfering substituent including $C_{1-4}$ alkyl and halide, and p is an integer from 0 to 4. Examples of such dialdehydes include glyoxal, glutaraldehyde, isophthalaldehyde and terephthalaldehyde.

The phenolic compound can be represented by formula (4):

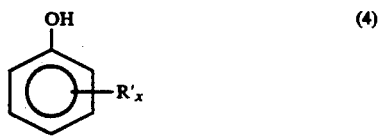

in which R' can be any substituent which does not interfere with the condensation reaction, including $C_{1-6}$ alkyl and halide, for example, and x is an integer from 0 to 4. Examples of such phenols include phenol, chlorophenol, fluorophenol and cresol.

The dialdehyde and the phenol are contacted in a reaction medium which includes an excess of phenol.

Generally, the starting reaction medium will contain an equivalent ratio of phenol to dialdehyde of at least about 8:1, preferably within the range of about 8:1 to about 25:1, most preferably about 10:1 to about 15:1. The excess phenol will generally serve as a reaction diluent and the amount can be adjusted depending upon the presence of other solvents or diluents in the reaction mixture and can be increased to help dilute the effect of excess water in the reaction.

In order to produce a mixed reaction product relatively high in the tetrakis species, the dialdehyde and the phenol are reacted in the presence of an acidic cation exchange resin catalyst. A number of cation exchange resins having acid sites are known and commercially available. Preferable cation exchange resins are slightly-crosslinked (0–4%) sulfonated styrene/divinylbenzene copolymers. Cation exchange resins can include those which have a portion of the acid sites neutralized by mercaptoamine moieties, although the unneutralized form is presently preferred for the preparation of tetraphenols. The presently preferred catalyst is a 2% divinylbenzene-crosslinked sulfonated polystyrene gellular resin. Such cation exchange resins are available from Rohm & Haas under the designation XE-561 and from Bayer under the designation Lewatit SC-102, for example.

In the production of a tetraphenol, a dialdehyde and an excess of phenol are fed to a reaction vessel containing the cation exchange resin catalyst. The reaction mixture is maintained at a temperature within the range of about 30° to about 110° C., preferably about 60° to about 95° C., for a time sufficient for preparation of a phenolic reaction product. The reaction product will contain biphenolic and triphenolic species as well as various isomers of the desired tetrakisphenol. The reaction is preferably carried out at atmospheric pressure. The reaction can be carried out in batch or continuous form. Under large-scale reaction conditions, continuous form will be preferred. The cation exchange resin catalyst can be used as a slurry with the reactants in batch reactions or in a fixed bed in a continuous process. Two or more staged additions of the dialdehyde with interstage water evaporation can be employed to enhance yields.

The phenol reactant can serve as a solvent for the reaction mixture. It is preferred, particularly for a continuous reaction, to carry out the reaction in the presence of an organic cosolvent, which has been found to promote the solubility of impurities which may be present in the starting dialdehyde. In a continuous process, the presence of the cosolvent can also prevent premature precipitation of the product or product intermediates as they form. Alcohols are the preferred organic cosolvents. Preferred alcohols, because of their availability and low cost, are $C_{1-8}$ alkanols such as methanol, isopropanol, ethanol and butanol, for example. If used, the cosolvent will generally be present in a weight ratio with respect to the dialdehyde of at least about 1:1, preferably within the range of about 1:1 to 10:1, most preferably about 1:1 to about 8:1.

The reaction time depends upon the reaction temperature and other reaction conditions. In a batch process, reaction time within the range of about 0.1 to 20 hours will generally achieve desired conversion. In a continuous operation using a fixed catalyst bed, a flow rate within the range of about 0.1 to 12.0, preferably 0.5 to 8, weight per hour per bed weight will generally be suitable.

The product solution is then separated from the solid catalyst, leaving a mixed reaction effluent containing a crude polyphenol, excess phenol, any cosolvent and water. This effluent is heated to a temperature effective to evaporate the cosolvent and water and, optionally, to evaporate some quantity of the excess phenol. In one embodiment of the invention process, the tetrakisphenol is crystallized by cooling the anhydrous phenolic medium. Highest yields of the desired tetrakisphenol fraction can be achieved in this embodiment by concentrating the crude polyphenol to about 5–30 weight percent in the phenol, preferably about 8 to about 20 percent, and cooling the solution to about 35° to about 80° C., preferably about 45° to about 55° C. with stirring.

In a second embodiment, a portion of the excess phenol is evaporated, an organic solvent is added, and tetrakisphenol is crystallized by cooling the solvent. For highest yields of the desired tetrakisphenol in this embodiment, the phenol content of the effluent is reduced so as to provide a solution which is 0 to about 30, usually about 10 to about 20, weight percent phenol, and then an organic solvent or solvent mixture is added. Suitable crystallization solvents include ketones such as acetone, methyl ethyl ketone and methyl isobutyl ketone, alcohols such as methanol and isopropanol, and aromatic hydrocarbons such as toluene. Acetone is the preferred crystallization solvent for highest yields. The solution, which may also contain solid tetrakisphenol which has precipitated from the concentrated phenol solution, is generally heated to reflux temperature for about 0.5 to about 1 hour and is then cooled. The optimum temperature of crystallization will vary depending upon the other crystallization conditions, such as the concentration of the crude polyphenol in the medium. To bring about crystallization, the solution is generally permitted to cool with stirring to about 35° to 55° C., preferably about 40° to about 50° C., or more rapid cooling can be effected by refrigeration, heat exchange, etc.

The recovered crystalline tetrakisphenol can optionally be treated in one or more subsequent recrystallization operations if additional selectivity is desired. In such a variation on the invention process, the recovered tetrakisphenol is dissolved in an organic solvent and recrystallized from the solvent as described above. Suitable recrystallization solvents include ketones such as acetone, methyl ethyl ketone and methyl isobutyl ketone, alcohols such as methanol and isopropanol, and aromatic hydrocarbons such as toluene. Solvent mixtures can be used. An illustration of such a recrystallization is provided in Example 2.

The crystalline tetrakisphenol can be recovered by conventional means such as filtration or centrifugation. The recovered solid can be washed with an organic liquid, preferably a ketone such as acetone or methyl ethyl ketone. The recovered tetrakisphenol can be used, for example, as a precursor of a low-chlorine epoxy resin for electronics applications. The mother liquor can be treated by conventional means, such as distillation under vacuum, for recovery of remaining polyphenolic species for use in preparing epoxy resins having less stringent low-chlorine requirements.

Figure 2:
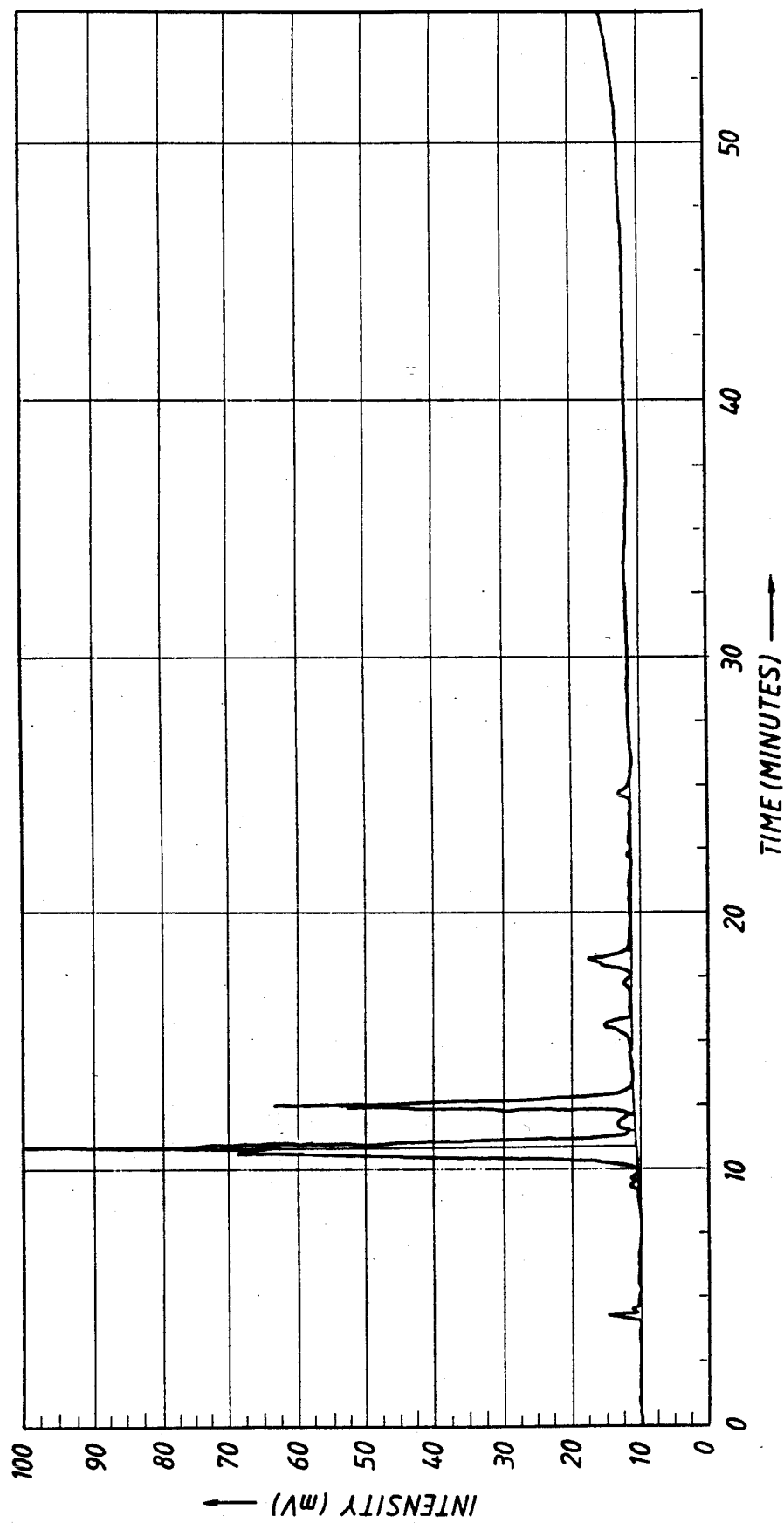
FIG. 2 is an HPLC of a crystallized polyphenolic reaction product containing predominately tetrakisphenolic species.
Figure 3:
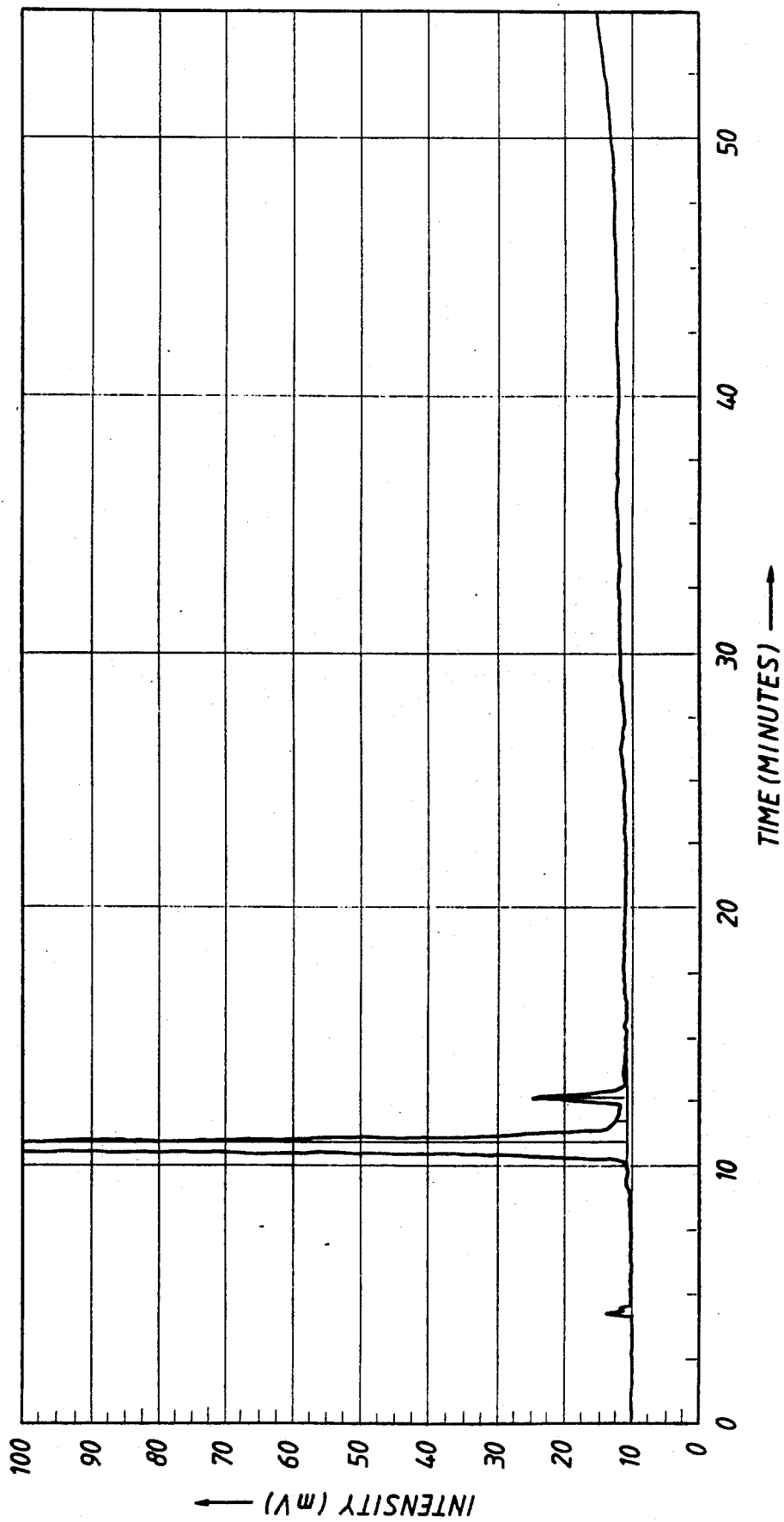
FIG. 3 is an HPLC of a recrystallized polyphenolic reaction product containing predominately tetrakisphenolic species.

Analysis of a typical crude TPE product by high performance liquid chromatograph (HPLC) is shown in FIG. 1. Several peaks have been identified as isomers of the tetra-functional tetrakisphenol of ethane (TKPE) by liquid chromatography-mass spectroscopy (LC-MS). The first group (about 11 minutes on the HPLC) consists of three isomers of tetrakis phenol (total area: A1), and the second group (about 13 minutes) consists of two isomers (total area: A2). (Depending on column elution efficiency, the two groups of isomers may sometimes appear as two peaks, respectively, consisting of the three and two isomers. The large peak at about 9.3 minutes in FIG. 1 is residual phenol.) FIG. 1 suggests that the crude product contains a significant amount of non-tetrakis by-products, while the crystallized products of FIGS. 2 and 3 are made up predominately of the desired tetrakis phenols.

EXAMPLE 1

1,1,2,2-tetrakis(hydroxyphenyl)ethane (TPE) was prepared as follows. To 1 part by weight of a 40 weight percent glyoxal solution were added 23.3 parts by weight phenol, 0.5 part methanol cosolvent and 4.1 parts Lewatit® SC-102, a 2% divinylbenzene-cross-linked, polystyrene-based, sulfonated gel cation exchange resin. The reaction mixture was maintained at about 80° C. for about 24 hours. The reaction product mixture was separated from the catalyst beads. Cosolvent methanol and by-product water were evaporated from the reaction product mixture. FIG. 1 is an HPLC of the crude product, which had a significant portion of non-tetrakis by-products. The ratio of A1 to A2 in the crude product was about 1.9.

The following procedures were used to recover the tetrakisphenol of ethane (TKPE) from the crude product mixture. In Experiment 1, the TKPE was crystallized directly from the excess phenol. In Experiments 2-6, the TKPE was crystallized from a mixture of phenol and acetone (Experiments 2-5) or from methanol (Experiment 6). The procedures of Experiments 2-6 involved adding to the crude polyphenol the indicated amount of crystallization solvent and heating the solution to reflux. The mixture was then cooled to the indicated temperature for crystallization, and the crystallized solid was separated from the filtrate. The solid was washed, dried and analyzed by HPLC.

Table 1 summarizes experimental conditions and results. These results illustrate the effectiveness of the invention process in isolating the desired tetrakis species in good yields. (FIG. 2 is an HPLC of the product of Experiment 3.)

TABLE 1

TKPE Crystallization
Starting Crude TPE, A1/A2 = 1.9

| Experiment | Solids g | PhOH g | Solvent g | Filtration Temp., °C. | Wash Solvent | Yield % | Product A1/A2 |
|---|---|---|---|---|---|---|---|
| 1 | 1 | 9.5 | 0 | 46 | MIBK | 36 | 17.1 |
| 2 | 3 | 1 | 3 (DMK) | 44 | DMK/H2O (50:50 w/w) | 52 | 2.4 |
| 3 | 10 | 1 | 9 (DMK) | 48 | DMK | 69 | 2.5 |
| 4 | 9.2 | 1 | 34.6 (DMK) | 41 | DMK | 50 | 2.5 |
| 5 | 7.1 | 1 | 12.2 (DMK) | 41 | DMK | 61 | 2.3 |
| 6 | 3 | 0.2 | 2 (MeOH) | 38 | MeOH | 27 | 8.7 |

DMK = acetone
MIBK = methyl isobutyl ketone
MeOH = methanol
PhOH = phenol

EXAMPLE 2

This example illustrates the embodiment of the invention process in which TKPE having a higher content of the first group of three isomers (i.e., higher A1/A2 ratio) is recovered. To a crystallized TKPE prepared as described in experiment 3 of Example 1 and essentially free of non-TKPE by-products was added the indicated amount of solvent or cosolvent mixture, and the solution was heated to reflux. The solution was then cooled to the indicated temperature for crystallization, and the solid was washed with the same solvent used for crystallization and then dried. The product was analyzed by HPLC. One such recrystallized product HPLC is shown in FIG. 3. Experimental conditions and results are shown in Table 2.

TABLE 2

TKPE Recrystallization

| Experiment | Starting A1/A2 | Solids g | Solvent g/type | Filtration Temp., °C. | Yield* % | Product A1/A2 |
|---|---|---|---|---|---|---|
| 7 | 2.5 | 2 | 3/MeOH | 42 | 16 | 20.5 |
| 8 | 2.5 | 1 | 0.8/MeOH | 42 | 26 | 16.4 |
| 9 | 2.5 | 1 | 0.55/MeOH | 42 | 39 | 6.6 |
| 10 | 2.9 | 1 | 2.5/MeOH:Tol (25:75 w/w) | 44 | 60 | 4.8 |

*Based on starting TKPE

I claim:
1. A process comprising:
(a) contacting, in a reaction mixture at a temperature within the range of about 30° to about 110° C., a dialdehyde of the formula

in which R is a direct bond or substituted or unsubstituted $C_{1-20}$ hydrocarbyl, and a stoichiometric excess of a phenolic compound which can be represented by the formula

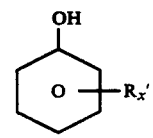

in which R' is selected from halide, $C_{1-6}$ alkyl and $C_{1-6}$ alkoxy, in the presence of a catalytic amount of an acid-functional ion exchange resin catalyst, to produce a mixed phenolic condensation product at least a portion of which is dissolved in the phenolic compound and by-product water;

(b) evaporating a major portion of the water; and (c) reducing the temperature of the phenolic compound to effect crystallization of a fraction of the mixed polyphenolic product relatively rich in tetrakisphenolic species.

2. The process of claim 1 in which step (a) is carried out in the presence of an organic solvent and step (b) involves evaporating the organic solvent.

3. The process of claim 1 in which the dialdehyde is selected from the group consisting of glyoxal, glutaraldehyde, isophthaldehyde and terephthalaldehyde.

4. The process of claim 3 in which the phenolic compound is present in the reaction mixture in an equivalent ratio to the dialdehyde of at least about 8:1.

5. The process of claim 4 in which the reaction temperature is within the range of about 60° to about 95° C.

6. The process of claim 5 in which the crystallization temperature is within the range of about 35° to about 80° C.

7. A process for preparing a tetraphenol of the formula

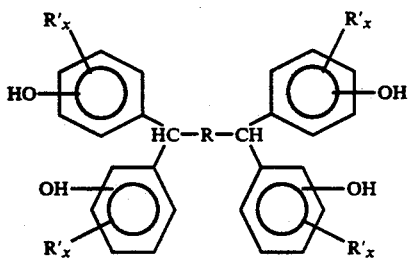

the process comprising:

(a) contacting, in a reaction mixture at a temperature within the range of about 30° to about 110° C., a dialdehyde of the formula

in which R is a direct bond or substituted or unsubstituted $C_{1-20}$ hydrocarbyl, and a stoichiometric excess of a phenolic compound which can be represented by the formula

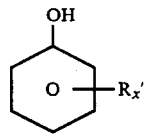

in which R' is selected from halide, $C_{1-6}$ alkyl and $C_{1-6}$ alkoxy, and x is an integer from 0 to 4, in the presence of a catalytic amount of an acid-functional ion exchange resin catalyst, to produce a reaction effluent comprising by-product water and a mixed polyphenolic condensation product at least partially dissolved in the phenolic compound;

(b) removing a least a portion of the phenol and at least a major portion of the water;

(c) dissolving at least a portion of the remaining reaction effluent in an organic solvent; and (d) reducing the temperature of the resulting solution to effect crystallization of a fraction of the mixed polyphenolic product relatively rich in tetrakisphenolic species.

8. The process of claim 7 in which the organic solvent of step (c) is selected from ketones, alcohols and aromatic hydrocarbons.

9. The process of claim 7 in which the organic solvent of step (c) comprises a ketone.

10. The process of claim 7 in which step (b) involves reducing the phenol content of the reaction effluent to an amount within the range of 0 to about 30 weight percent of the remaining reaction effluent.

11. The process of claim 7 in which step (c) involves heating the resulting solution at reflux temperature for at least about 0.5 hour.

12. The process of claim 7 in which the dialdehyde is glyoxal.

13. The process of claim 12 in which the phenolic compound is phenol.

14. The process of claim 7 which further comprises (e) redissolving the crystallized fraction in a second organic solvent and cooling the resulting solution to effect recrystallization of a solid polyphenol fraction.

15. The process of claim 14 in which the solvent for step (e) comprises an alcohol.

16. The process of claim 14 in which the solvent for step (e) comprises methanol.

* * * * *